US012763211B2

(12) United States Patent
Helm et al.

(10) Patent No.: US 12,763,211 B2
(45) Date of Patent: Oct. 13, 2026

(54) SYSTEM AND METHOD FOR IMAGING

(71) Applicant: Medtronic Navigation, Inc., Lafayette, CO (US)

(72) Inventors: Patrick A. Helm, Canton, MA (US); Andrew Wald, Fort Worth, TX (US); Shai Ronen, Westminster, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 0 days.

(21) Appl. No.: 18/679,392

(22) Filed: May 30, 2024

(65) Prior Publication Data

US 2024/0321454 A1 Sep. 26, 2024

Related U.S. Application Data

(63) Continuation of application No. 16/356,690, filed on Mar. 18, 2019, now Pat. No. 12,051,505.

(51) Int. Cl.

| | |
|---|---|
| ***A61B 34/10*** | (2016.01) |
| ***A61B 34/00*** | (2016.01) |
| ***A61B 34/20*** | (2016.01) |
| ***G06N 3/08*** | (2023.01) |
| ***G16H 50/20*** | (2018.01) |
| *G06T 7/11* | (2017.01) |

(52) U.S. Cl.

CPC ............ *G16H 50/20* (2018.01); *A61B 34/10* (2016.02); *A61B 34/20* (2016.02); *A61B 34/25* (2016.02); *G06N 3/08* (2013.01); *A61B 2034/105* (2016.02); *A61B 2034/107* (2016.02); *A61B 2034/2051* (2016.02); *A61B 2034/2057* (2016.02); *A61B 2034/2065* (2016.02); *A61B 2034/256* (2016.02); *G06T 7/11* (2017.01); *G06T 2207/20081* (2013.01); *G06T 2207/20084* (2013.01)

(58) Field of Classification Search

CPC ............ G06T 2207/20081; G06T 7/11; A61B 2034/105; A61B 2034/107; A61B 2034/2051; A61B 2034/2057; A61B 2034/2065; A61B 2034/256; A61B 34/25; A61B 34/10; A61B 34/20

See application file for complete search history.

(56) References Cited

U.S. PATENT DOCUMENTS

| | | | |
|---|---|---|---|
| 7,697,972 | B2 | 4/2010 | Verard et al. |
| RE44,305 | E | 6/2013 | Foley et al. |

(Continued)

FOREIGN PATENT DOCUMENTS

| | | | |
|---|---|---|---|
| CN | 102542302 | A | 7/2012 |
| CN | 109414295 | A | 3/2019 |

(Continued)

OTHER PUBLICATIONS

European Office Action for related European Application No. 20718922.6; dated: Nov. 13, 2024; 9 pages.

(Continued)

*Primary Examiner* — Patricia J Park

(74) *Attorney, Agent, or Firm* — Harrity & Harrity, LLP

(57) ABSTRACT

An image segmentation system and display is disclosed. The system may be operated or configured to generate a segmentation of a member from an image. The image and/or the segmentation may be displayed for viewing by a user.

20 Claims, 7 Drawing Sheets

(56) References Cited

U.S. PATENT DOCUMENTS

| | | | |
|---|---|---|---|
| 8,644,907 B2 | 2/2014 | Hartmann et al. | |
| 8,842,893 B2 | 9/2014 | Teichman et al. | |
| 2004/0199072 A1 | 10/2004 | Sprouse et al. | |
| 2012/0106821 A1 | 5/2012 | Madabhushi et al. | |
| 2013/0085344 A1 | 4/2013 | Merkl et al. | |
| 2014/0023290 A1 | 1/2014 | Barth et al. | |
| 2014/0171781 A1 | 6/2014 | Stiles | |
| 2017/0011535 A1* | 1/2017 | Abkai | A61B 6/032 |
| 2017/0316561 A1* | 11/2017 | Helm | G06F 3/04817 |
| 2019/0029757 A1 | 1/2019 | Roh et al. | |
| 2019/0065970 A1* | 2/2019 | Bonutti | G16H 20/10 |
| 2019/0133693 A1 | 5/2019 | Mahfouz | |
| 2019/0146458 A1* | 5/2019 | Roh | G05B 19/4099 700/98 |
| 2019/0295240 A1 | 9/2019 | Doutre et al. | |
| 2019/0325574 A1 | 10/2019 | Jin et al. | |
| 2019/0336108 A1 | 11/2019 | Hope Simpson et al. | |
| 2020/0178927 A1* | 6/2020 | Patton | A61B 8/0841 |
| 2020/0281728 A1 | 9/2020 | Kulper et al. | |
| 2021/0401407 A1* | 12/2021 | Yang | A61B 8/0841 |

FOREIGN PATENT DOCUMENTS

| | | |
|---|---|---|
| CN | 109447940 A | 3/2019 |
| WO | 2018118919 A1 | 6/2018 |

OTHER PUBLICATIONS

Cicek, et al., 3D U-Net: Learning Dense Volumetric Segmentation from Sparse Annotation, 2016, 8 pgs.
Ioffe, et al., Batch Normalization: Accelerating Deep Network Training by Reducing Internal Covariate Shift, 2015, 11 pgs.
Dumoulin, et al., A guide to convolution arithmetic for deep learning, 2018, 31 pgs.
Zheng et al: "Deep learning with limited labeled image data for health informatics", Jan. 1, 2018, XP055699017.
Sahiner et al: "Deep learning in medical imaging and radiation thereapy", Medical Physics, vol. 46, No. 1, Nov. 20, 2018, pp. e1-e36, XP055698991, US; ISSN: 0094-2405, DOI: 10.1002/mp.13264.
International Search Report and Written Opinion mailed Jun. 8, 2020 in corresponding/related International Application No. PCT/US2020/022998.
International Search Report and Written Opinion mailed Jun. 8, 2020 in corresponding/related International Application No. PCT/US2020/023005.
Esfandiari et al: "A deep learning framework for segmentation and pose estimation of pedicle screw implants based on C-arm fluoroscopy", International Journal of Computer Assisted Radiology and Surgery, Springer, DE, vol. 13, No. 8, May 28, 2018, pp. 1269-1282, XP036559997, ISSN: 1861-6410, DOI: 10.1007/S11548-018-1776.9 [retrieved on May 28, 2018].
Miao et al: "A CNN Regression Approach for Real-Time 2D/3D Registration", IEEE Transactions on Medical Imaging, IEEE Service Center, Piscataway, NJ, US, vol. 35, No. 5, May 1, 2016, pp. 1352-1363, XP011607918, ISSN: 0278-0062, DOI: 10.1109/TMI.2016.2521800 [retrieved Apr. 29, 2016].
Popescu et al: "Competitive Hopfield Neural Network Model for Evaluating Pedicle Screw Placement Accuracy", Strojniski Vestnik—Journal of Mechanical Engineering, vol. 58, No. 9, Sep. 15, 2012, XP055697850, SI; ISSN: 0039-2480, DOI: 10.5545/sv-jme.2011.184.
International Preliminary Report on Patentability regarding International Application No. PCT/US2020/023005, dated Sep. 16, 2021.
Esfandiari Hooman et al: "A deep learning framework for segmentation and pose estimation of pedicle screw implants based on Carm fluoroscopy", International Journal of Computer Assisted Radiology and Surgery, Springer, DE, vol. 13, No. 8, May 28, 2018 (May 28, 2018), pp. 1269-1282, XP036559997, ISSN: 1861-6410, DOI: 10.1007/S11548-018-1776-9 [retrieved on May 28, 2018].
Miao Shun et al: "A CNN Regression Approach for Real-Time 2D/3D Registration", IEEE Transactions on Medical Imaging, IEEE Service Center, Piscataway, NJ, US, vol. 35, No. 5, May 1, 2016 (May 1, 2016), pp. 1352-1363, XP011607918, ISSN: 0278-0062, DOI: 10.1109/TMI.2016.2521800 [retrieved on Apr. 29, 2016].
Diana Popescu et al: "Competitive Hopfield Neural Network Model for Evaluating Pedicle Screw Placement Accuracy", Strojniski Vestnik—Journal of Mechanical Engineering, vol. 58, No. 9, Sep. 15, 2012 (Sep. 15, 2012), pp. 509-516, XP055697850, SI ISSN: 0039-2480, DOI: 10.5545/sv-jme.2011.184.
International Preliminary Report on Patentability regarding International Application No. PCT/US2020/022998, mailed Sep. 16, 2021.
Jiannan Zheng et al: "Deep learning with limited labeled image data for health informatics", Jan. 1, 2018 (Jan. 1, 2018), XP055699017.
Berkman Sahiner et al: "Deep learning in medical imaging and radiation therapy", Medical Physics., vol. 46, No. 1, Nov. 20, 2018 (Nov. 20, 2018), pp. e1-e36, XP055698991, USISSN: 0094-2405, DOI: 10.1002/mp.13264.
Mei, Xiao-Liang, et al., Accuracy of Percutaneous Pedicle Screw Insertion in Thoracic and Lumbar Spine by Computer Tomography Assessment, Journal of Clinical Orthopaedics, Oct. 2015; 18( 5), pp. 529-531.
Wu, M., "Rehabilitation Nursing," Tongji University Press, Feb. 28, 2015, pp. 1-6.
European Office Action for related European Application No. 20718919.2; dated: Jan. 22, 2025; 9 pages.
Chinese Office Action for related Chinese Application No. 202080021981.1; dated: Jan. 24, 2025; 17 pages.
Esfandiari, H. "A Deep Learning Framework For Segmentation And Pose Estimation Of Pedicle Screw Implants Based On C-Arm Fluoroscopy", International Journal of Computer Assisted Radiology and Surgery, (2018), 11-18.
Popescu, D., "Competitive Hopfield Neural Network Model for Evaluating Pedocle Screw Placement Accuracy", Journal of Mechinical Engineering (2012), 9 pages.
Chinese Office Action for related Chinese Application No. 202080021817.0; Dated: Sep. 29, 2024; 24 pages.
Second Chinese Office Action for related Chinese Application No. 202080021817.0 dated Feb. 28, 2025, 5 pages.

* cited by examiner

SYSTEM AND METHOD FOR IMAGING

CROSS-REFERENCE TO RELATED APPLICATIONS

The application is a continuation of U.S. application Ser. No. 16/356,690 filed on Mar. 18, 2019. The entire disclosure of the above application is incorporated herein by reference.

This application includes subject matter similar to that disclosed in filed U.S. patent application Ser. No. 16/356,729 filed Mar. 18, 2019. The entire disclosure of the above application is incorporated herein by reference.

FIELD

The subject disclosure relates generally to a system and method for determining a position, including location and orientation, of a member in space relative to a subject and identifying features in an image.

BACKGROUND

This section provides background information related to the present disclosure which is not necessarily prior art.

A procedure performed on a subject, such as a human subject, may include a placement of an element within the subject. In various procedures, however, an open viewing or easy access of an entire portion of a subject is impractical or impossible. In various circumstances, therefore, image data is acquired of the subject such as x-ray image data or other image data. A user may view the image data to attempt to analyze and determine the position of the placed item within the subject. Viewing the image may include viewing an implant that has been positioned within the subject and image data regarding the subject itself. In various instances, however, distortion may be introduced and/or overlap of imageable parts may occur. Accordingly, analyzing an image may require analysis of the image to identify the portions relating to the positioned member and the remaining parts of the subject. To assist in performing a procedure, a tracking system may be used. The tracking system may include or generate an electro-magnetic field that may be generated with a plurality of coils, such as three orthogonally placed coils. Various transmitter or field generation systems include the AxiEM™ electro-magnetic navigation system sold by Medtronic Navigation, Inc., having a place of business in Louisville, Colorado. The AxiEM™ electro-magnetic navigation system may include a plurality of coils that are used to generate an electro-magnetic field that is sensed by a tracking device, which may be the sensor coil, to allow a navigation system, such as a StealthStation® surgical navigation system, to be used to track and/or illustrate a tracked position of an instrument.

The tracking system may also, or alternatively, include an optical tracking system. Optical tracking systems include those such as the StealthStation® S7® tracking system. The optical tracking system includes a set of cameras with a field of vision to triangulate a position of the instrument.

SUMMARY

This section provides a general summary of the disclosure, and is not a comprehensive disclosure of its full scope or all of its features.

A system to assist in performing a procedure and or analyzing a procedure is disclosed. The procedure may be performed on a living subject such as an animal, human, or other selected patient. The procedure may also include any other appropriate type of procedure, such as one being performed on an inanimate object (e.g. an enclosed structure, airframe, chassis, etc.). Nevertheless, the procedure may be performed using a navigation system where a tracking system is able to track a selected one or more items.

The procedure may include the placing of an implant within a subject, such as in a human subject. In various embodiments, the member or implant may be a pedicle screw, a spinal rod, a joint implant, or other selected implants. In performing an implant procedure, a member or implant is positioned within a subject and is selected to be placed at an appropriate or selected position. After placement of an implant, however, it may be desirable to confirm that a positioned or post-procedure position of the implant matches or achieves a selected result.

In various embodiments, determining a placement of an implant may require access to or viewing portions of a subject that are not within a field of view of an incision or cut of a subject. Here also, as discussed above, various features of human subject may also block or obstruct a visual view of an internal portion. Accordingly, an image may be acquired of a subject including the positioned implant member, such as with an x-ray or other imaging system. Due to the imaging modalities, however, determining the implant relative to other portions of the subject may include analyzing the image data. Various automatic techniques, according to various embodiments, may be used to identify the implant and/or the portions of the subject for performing an analysis of the position of the implant. For example, segmenting an implant from other portions of the image may be selected to confirm or determine a placement of the implant within the subject.

The details of one or more aspects of the disclosure are set forth in the accompanying drawings and the description below. Other features, objects, and advantages of the techniques described in this disclosure will be apparent from the description and drawings, and from the claims.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
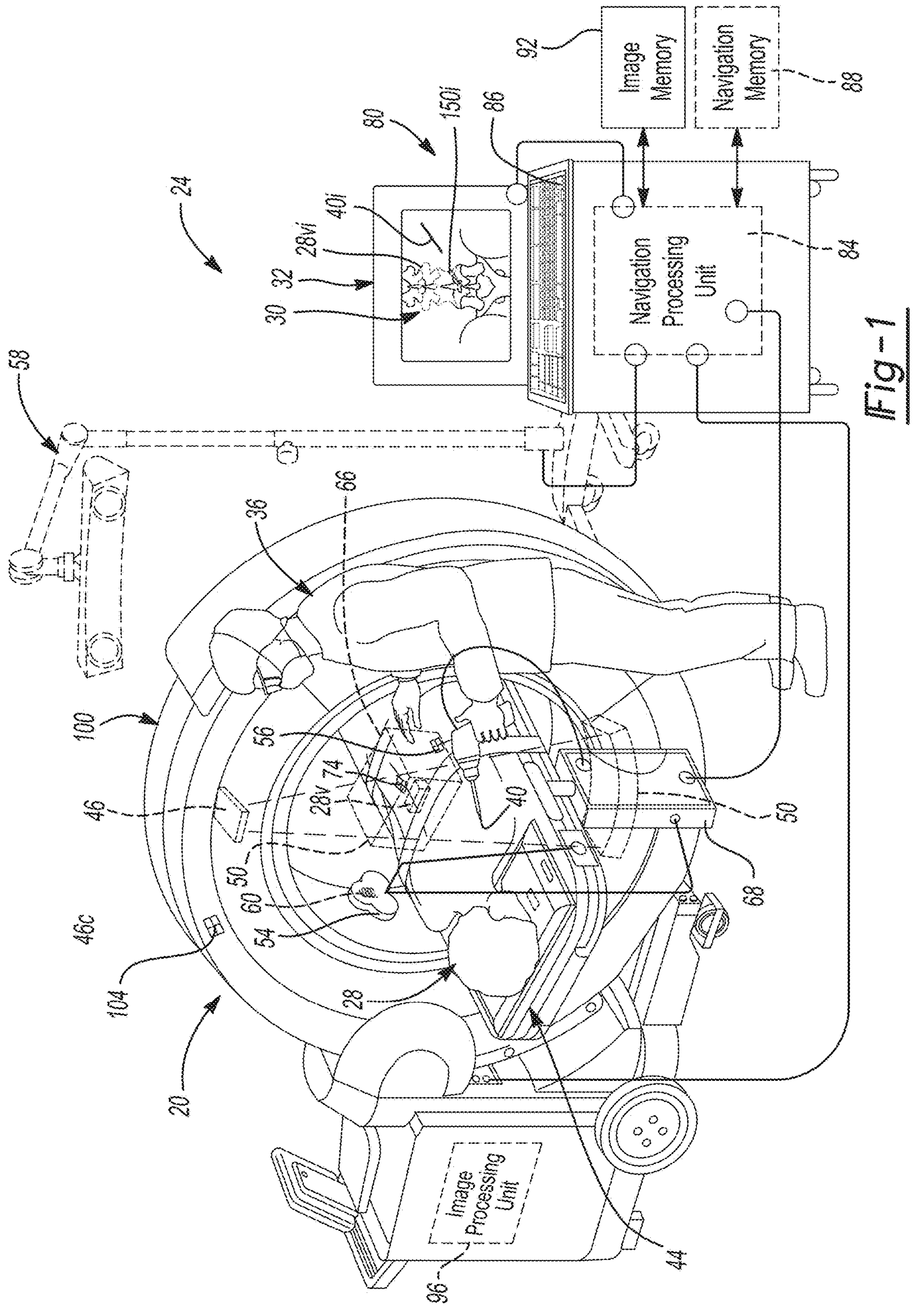
FIG. 1 is an environmental view of a navigation system.

With reference to FIG. 1, an environmental view of an operating room with an imaging system 20 that may be used with a navigation system 24 is illustrated. The imaging system 20 may be used to image a subject 28. The imaging system 20 may acquire images of the subject 28 at selected times during a procedure. In various embodiments, the imaging system 20 may acquire image data to display and/or generate an image 30 of the subject 28 for display with the display device 32.

The navigation system 24 may be used for various purposes or procedures by one or more users, such as a user 36. The navigation system 24 may be used to determine or track a position of an instrument 40 (e.g. powered tool, implant, etc.) in a volume. The position may include both a three dimensional X, Y, Z location and orientation. Orientation may include one or more degrees of freedom, such as three degrees of freedom. It is understood, however, that any appropriate degree of freedom position information, such as less than six-degree of freedom position information, may be determined and/or presented to the user 36.

Tracking the position of the instrument 40 may assist the user 36 in determining a position of the instrument 40, even if the instrument 40 is not directly viewable by the user 36. Various procedures may block the view of the user 36, such as performing a repair or assembling an inanimate system, such as a robotic system, assembling portions of an airframe or an automobile, or the like. Various other procedures may include a surgical procedure, such as performing a spinal procedure, neurological procedure, positioning a deep brain simulation probe, or other surgical procedures on a living subject. In various embodiments, for example, the living subject may be a human subject 28 and the procedure may be performed on the human subject 28. It is understood, however, that the instrument 40 may be tracked and/or navigated relative to any subject for any appropriate procedure. Tracking or navigating an instrument for a procedure, such as a surgical procedure, on a human or living subject is merely exemplary.

Nevertheless, in various embodiments, the surgical navigation system 24, as discussed further herein, may incorporate various portions or systems, such as those disclosed in U.S. Pat. Nos. RE44,305; 7,697,972; 8,644,907; and 8,842,893; and U.S. Pat. App. Pub. No. 2004/0199072, all incorporated herein by reference. Various components or systems may be used in combination with or incorporated with the navigation system 24, such as the imaging system 20. It is understood, however, that the imaging system 20 may be used separate and independent of the navigation system 24.

The imaging system 20 operable to image the subject 28 can include, an O-arm® imaging system, magnetic resonance imaging (MRI) system, computed tomography system, etc. A subject support 44 may be used to support or hold the subject 28 during imaging and/or during a procedure. The same or different supports may be used for different portions of a procedure.

In various embodiments, the imaging system 20 may include a source 46. The source 46 may emit and/or generate X-rays. The X-rays may form a cone 46*c*, such as in a cone beam, that impinge on the subject 28. Some of the X-rays pass though and some are attenuated by the subject 28. The imaging system 20 may further include a detector 50 to detect the X-rays that are not completely attenuated, or blocked, by the subject 28. Thus, the image data may include X-ray image data. Further, the image data may be two-dimensional (2D) image data.

Image data may be acquired, such as with one or more of the imaging systems 20 discussed above, during a surgical procedure, prior to a surgical procedure, or subsequent to a procedure for displaying the image 30 on the display device 32. In various embodiments, the acquired image data may also be used to form or reconstruct selected types of image data, such as three-dimensional volumes, even if the image data is 2D image data. In various embodiments, as discussed herein, the image data may include various portions (e.g. the instrument 40) that is within the image 30. Selected processor systems, as discussed herein, may be used to segment the instrument 40 from other portions within the image 30, as also discussed herein.

The instrument 40 may be tracked in a trackable volume or a navigational volume by one or more tracking systems. Tracking systems may include one or more tracking systems that operate in an identical manner or more and/or different manner or mode. For example, the tracking system may include an electro-magnetic (EM) localizer 54, as illustrated in FIG. 1. In various embodiments, it is understood by one skilled in the art, that other appropriate tracking systems may be used including optical (including an optical or camera localizer 58), radar, ultrasonic, etc. The discussion herein of the EM localizer 54 and tracking system is merely exemplary of tracking systems operable with the navigation system 24. The position of the instrument 40 may be tracked in the tracking volume relative to the subject 28 and then illustrated as a graphical representation or graphical overlay, also referred to as an icon 40*i* with the display device 32. In various embodiments, the icon 40*i* may be superimposed on the image 30 and/or adjacent to the image 30. As discussed herein, the navigation system 24 may incorporate the display device 30 and operate to render the image 30 from selected image data, display the image 30, determine the position of the instrument 16, determine the position of the icon 40*i*, etc.

With reference to FIG. 1, the EM localizer 54 is operable to generate electro-magnetic fields with an included transmitting coil array (TCA) that includes one or more transmitting conductive coils 60 which is incorporated into the localizer 54. The localizer 54 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electro-magnetic fields generated will extend away from the localizer 54 and form a navigation domain or volume 66, such as encompassing all or a portion of a head, spinal vertebrae 28*v*, or other appropriate portion. The coils may be powered through a TCA controller and/or power supply 68. It is understood, however, that more than one of the EM localizers 54 may be provided and each may be placed at different and selected locations.

The navigation domain or volume 66 generally defines a navigation space or patient space. As is generally understood in the art, the instrument 40, such as a drill, lead, implant (e.g. screw) etc., may be tracked in the navigation space that is defined by a navigation domain relative to a patient or subject 28 with an instrument tracking device 70. For example, the instrument 40 may be freely moveable, such as by the user 36, relative to a dynamic reference frame (DRF)

or patient reference frame tracker 74 that is fixed relative to the subject 28. Both the tracking devices 70, 74 may include tracking portions that are tracking with appropriate tracking systems, such as sensing coils (e.g. conductive material formed or placed in a coil) that senses and are used to measure a magnetic field strength, optical reflectors, ultrasonic emitters, etc. Due to the instrument tracking device 70 connected or associated with the instrument 16, relative to the DRF 74, the navigation system 24 may be used to track the position of the instrument 40 relative to the DRF 74.

The navigation volume or patient space may be registered to an image space defined by the image 30 of the subject 28 and the icon 40*i* representing the instrument 40 may be illustrated at a navigated (e.g. determined) and tracked position with the display device 32, such as superimposed on the image 30. Registration of the patient space to the image space and determining a position of a tracking device, such as with the tracking device 70, relative to a DRF, such as the DRF 74, may be performed as generally known in the art, including as disclosed in U.S. Pat. Nos. RE44,305; 7,697,972; 8,644,907; and 8,842,893; and U.S. Pat. App. Pub. No. 2004/0199072, all incorporated herein by reference.

The navigation system 24 may further include a navigation processor system 80. The navigation processor system 80 may include the display device 32, the localizer 54, the TCA controller 68, and other portions and/or connections thereto. For example, a wire connection may be provided between the TCA controller 68 and a navigation processing unit 84. Further, the navigation processor system 80 may have one or more user control inputs, such as a keyboard 86, and/or have additional inputs such as from communication with one or more navigation memory systems 88, either integrated or via a communication system. Additional and/or alternative memory systems 92 may also be accessed including analysis memory that may include image memory, model (e.g. computer aided drafting (CAD) models having dimensions and materials, known component (e.g. x-ray attenuation relative to material information)), etc. The navigation processor system 80 may, according to various embodiments include those disclosed in U.S. Pat. Nos. RE44,305; 7,697,972; 8,644,907; and 8,842,893; and U.S. Pat. App. Pub. No. 2004/0199072, all incorporated herein by reference, or may also include the commercially available StealthStation® or Fusion™ surgical navigation systems sold by Medtronic Navigation, Inc. having a place of business in Louisville, CO.

Tracking information, including information regarding the electro-magnetic fields sensed with the tracking devices 70, 74 may be delivered via a communication system, such as the TCA controller 68, which also may be a tracking device controller, to the navigation processor system 80 including the navigation processor 84. Thus, the tracked position of the instrument 40 may be illustrated as the icon 40*i* relative to the image 30. Various other memory and processing systems may also be provided with and/or in communication with the processor system 80, including the memory system 88 that is in communication with the navigation processor 84 and/or an imaging processing unit 96.

The image processing unit 96 may be incorporated into the imaging system 20, such as the O-arm® imaging system, as discussed above. The imaging system 20 may include various additional portions such as a gantry 100 within which the source 46 and the x-ray detector 50 are moveable. The imaging system 20 may also be tracked with a tracking device 104. It is understood, however, that the imaging system 20 need not be present while tracking the tracking devices, including the instrument tracking device 40. Further, the imaging system 20 need not be present in an operation or procedure room. The illustration including the imaging system 20 is merely for the present disclosure and it is understood that the imaging system 20 and/or the subject 28 may be moved for a selected image acquisition procedure before, after, or during a selected procedure. Also, the imaging system 20 may be any appropriate imaging system including a MRI, CT, etc.

The image 30 that is displayed with the display device 32 may be based upon image data that is acquired of the subject 28 in various manners. For example, the imaging system 24 may be used to acquire image data that is used to generate the image 30. It is understood, however, that other appropriate imaging systems may be used to generate the image 30 using image data acquired with the selected imaging system. Imaging systems may include magnetic resonance imagers, computed tomography imagers, and other appropriate imaging systems. Further the image data acquired may be two dimensional or three dimensional data and may have a time varying component, such as imaging the patient during a heart rhythm and/or breathing cycle.

In various embodiments, the image data is a 2D image data that is generated with a cone beam. The cone beam that is used to generate the 2D image data may be part of an imaging system, such as the O-arm® imaging system. The 2D image data may then be used to reconstruct a 3D image or model of the imaged subject, such as the subject 28. The reconstructed 3D image and/or an image based on the 2D image data may be displayed. Thus, it is understood by one skilled in the art that the image 30 may be generated using the selected image data, such as from the imaging system 20.

Figure 2:
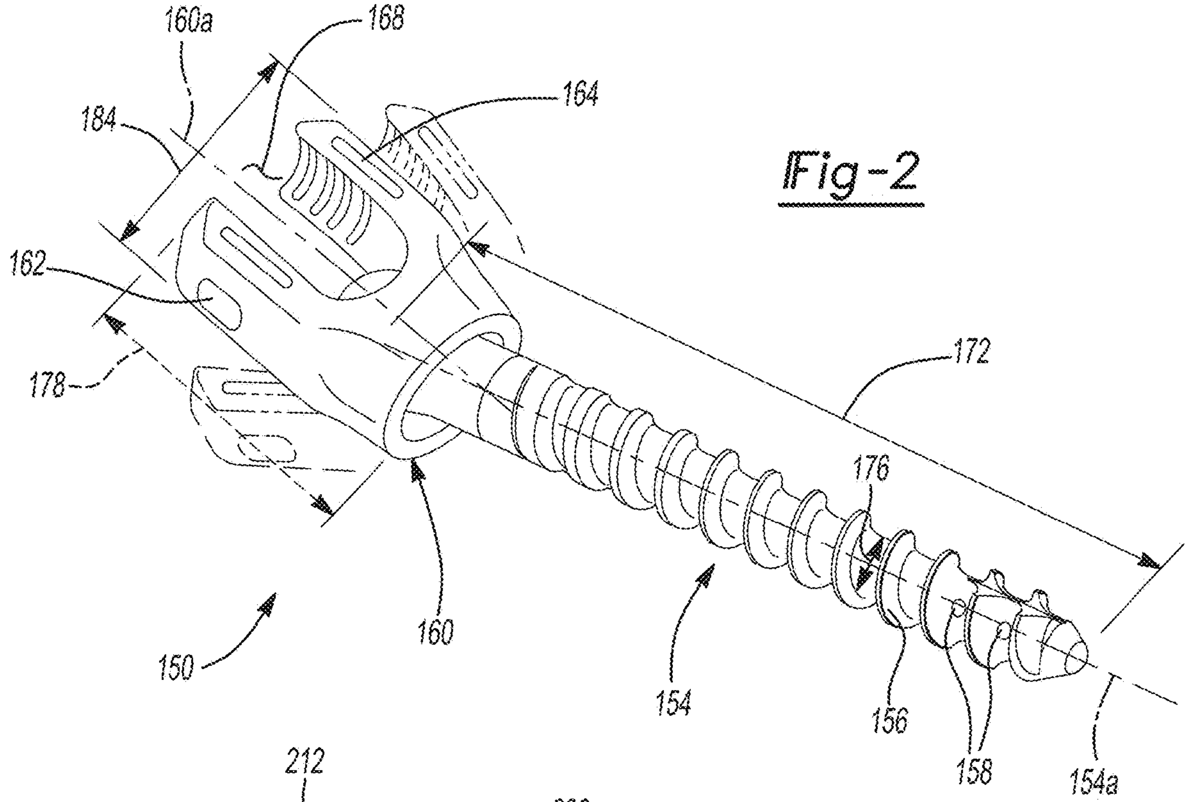
FIG. 2 is a view of a three-dimensional (3D) model of a member, according to various embodiments.

In addition, the image 30 may be segmented, for various purposes, including those discussed further herein. Segmentation of the image 30 may be used to determine and/or delineate objects or portions in the image 30. The delineation may include or be made as a mask that is represented on the display 32. The representation may be shown on the display such as with a graphical representation or a graphical overlay of the mask. The segmentation of the image 30, as is generally understood by one skilled in the art, may be to label or identify objects within the image In various embodiments, the segmentation, also referred to as the delineation, may be used to identify boundaries of various portions within the image 30, such as boundaries of one or more structures of the subject 28 and/or implants placed with the subject 28, such as the instrument 40. As discussed above, the instrument 40 may include an implant, such as a screw. As illustrated in FIG. 2, in various embodiments, a screw may include a screw such as a CD Horizon® Solara® Fenestrated Screws or a CD Horizon® Solara® Spinal System Screws, both sold by Medtronic, Inc. having a place of business in Minnesota, USA. It is understood, however, that other appropriate implants may also implanted in the subject 28 and may also be imaged, including joint replacement implants, deep brain stimulation probes, etc. The discussion herein of the pedicle screw 150 is merely exemplary for the subject disclosure.

The image 30 is generated from image data of the subject 28 that is acquired with the imaging system 20. In various embodiments, the image data that is used to generate the image 30 may include image data of the screw 150. The screw 150, for example, may be implanted in the subject 28. As is understood by one skilled in the art, an image of the subject 28 may be acquired or generated after placing the screw 150, or more than one screw 150, in the subject 28. The image data acquired of the subject after placing the screw 150 may be to confirm and/or evaluate the position of the screw 150 in the subject 28. In various embodiments, it is understood by one skilled in the art, that the image data and/or resulting or generated image 30 may be used to confirm the placement of any appropriate member or item including a screw or beam in an airframe, automobile, bridge span, etc. Thus, the screw 150 is merely exemplary.

Accordingly, the image 30 may include a first vertebrae **28*vi* image of a vertebrae 28*v*. Further, the image 30 may include an implant or screw image 150*i* (which may be the instrument 40, as discussed above). The screw image 150*i* may be further delineated or segmented, as discussed herein, and a screw graphical representation 150*i*' may be displayed relative to the image 30 as illustrated in FIG. 3. The screw graphical representation 150*i*' may be used by the user 36** for various purposes, as also discussed herein.

According to various embodiments, the image 30 may be segmented in a substantially automatic manner. In various embodiments, the automatic segmentation may be incorporated into a neural network. The neural network may be designed to learn or determine selected weights for activating different neurons in the network for identifying features, and applications such as segmenting an item in an image. Neural networks include various types of networks, such as a convolutional neural network (CNN). The CNN may be taught or learn to determine, such as with a probability or prediction, various features in the image 30 (and/or the image data used to generate the image 30), according to various embodiments. Various features may include objects such as the screw 150 and/or portions thereof, such as with segmentations or boundaries of these objects or portions. The selected segmentations may include identifying a segmentation of the screw 150 in the image, and may further include segmenting separate portions of the screw 150.

As illustrated in FIG. 2, the screw 150 may include two or more portions. The screw 150 may include a shaft 154 that has a thread 156. The shaft 154 may extend along a long axis **154*a*. The shaft 156 is selected to be placed within the vertebrae 28*v*. The screw 150 may further include a head or petal portion 160. The head portion 160 generally extends along a long axis 160*a*. The head 160 is configured to move relative to the shaft 154, before or after implantation of the screw 150, thus changing or selecting the orientation of the axes 154*a*, 160*a*. The head 160 may be rotated and/or angled relative to the shaft 154. The head 160 includes a first side 162 and a second side 164 with a passage or trough 168 there between. A cap or locking portion (not illustrated) may be placed between the first side 162 and second side 164 to lock a rod within the trough. The rod may be positioned between two or more of the screws 150 within the subject 28**.

The screw 150, including the shaft 154 and the head 160 may also be formed of different materials. For example, the shaft 154 may be formed of a first selected metal or metal alloy and the head 160 may be formed of the same or different material, such as a second different metal or metal alloy. In various embodiments, the shaft 154 and the head 160 may be formed of the same material, but it is also understood that the shaft 154 and the head 160 may be formed of different materials. For example, the shaft 154 may be formed of titanium or titanium alloy and the head 160 may be formed of a steel alloy, such as a stainless steel alloy.

Regardless of the materials from which the screw 150 is formed, the materials may have a specific or known attenuation properties (e.g. absorption or scattering) in various imaging modalities. For example, the shaft 154 formed of a selected material (e.g. titanium) may have known attenuation characteristics regarding specific or selected bands of x-rays. Further the head 160 may also include know attenuation characteristics. Thus, the screw 150 may have known imaging characteristics, such as x-ray attenuation characteristics. Various known or predetermined characteristics may include known components of the imaging qualities of the screw 150. Selected known techniques for identifying effects of selected materials are described in U.S. Pat. Application Publication No. 2017/0316561, incorporated herein by reference. The various interactions of materials with x-rays may be described by techniques such as the x-ray scatter and beam hardening Further, the screw 150 may include selected or known geometries, sizes, and configurations. For example, the shaft 154 may have a known length or dimension 172. Further the shaft 154 may include a known width or diameter dimension 176. The dimensions of the thread 156 absolutely and relative to the shaft 154 may also be known. The geometry of the shaft 154, including the length 172, width 176 and thread dimensions may be saved as a part of a model, such as a computer aided design (CAD) model of the screw 150. Further the head 160 may include dimensions, such as a height or length 178 and a width 184. The head dimensions 178, 184 may also be known or saved in the CAD model, such as relative to the shaft 154. The model may include one or more specific or known orientations of the head 160 relative to the shaft 154. Accordingly, the model may include dimensions and geometries of the screw 150, including the respective geometries of the shaft 154 and the head 160 and also known or possible orientations of the head 160 relative to the shaft 154. It is understood, however, that the model may include features, such as possible multiple materials of the screw 150, flexibility of the screw 150, or other features.

A combination of the geometries of the screw 150 and materials of the screw 150 may be incorporated into the model. The model, therefore, may be used to generate a simulated image that is a known or expected image of the screw when placed in an x-ray beam and x-rays are detected by a detector with the screw in the x-ray beam. The generated image is a simulated image of the screw 150 (or any appropriate member), as discussed herein, that would simulate a type of imaging modality (e.g. x-ray imaging, magnetic resonance imaging, etc.). The generated simulated image may, then, be incorporated into an image that is captured with a similar or identical modality. In other words, the generated simulated image that simulates x-ray images may be overlayed on a x-ray image acquired with an imaging system that uses the x-ray modality.

Figure 3A:
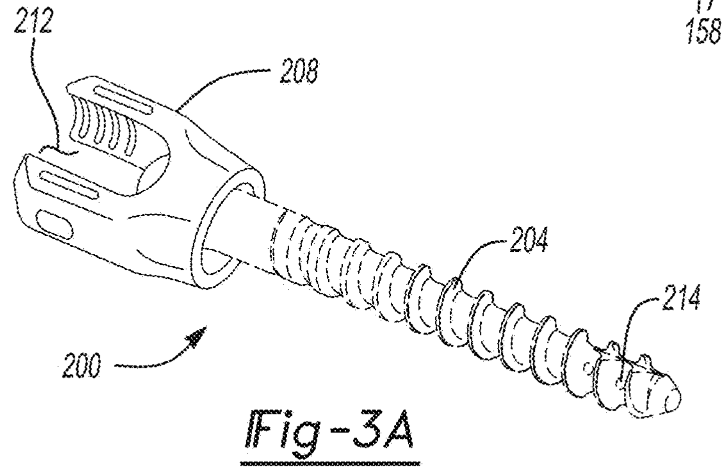
FIG. 3A and FIG. 3B are alternative views of generated simulated images of the model of FIG. 2, according to various embodiments.
Figure 3B:
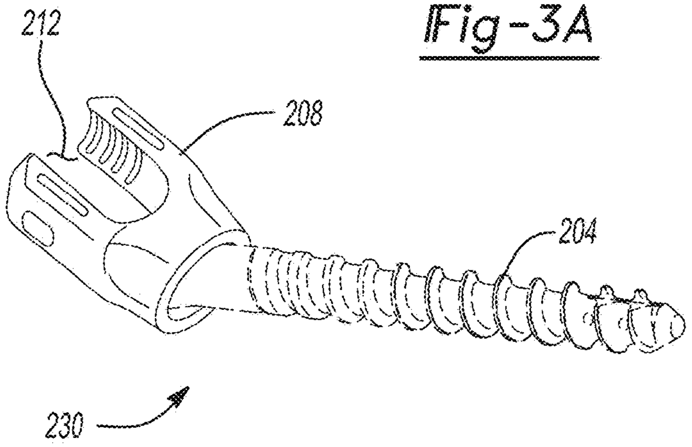

As illustrated in FIG. 2, the screw 150 may include various portions and features. These portions and features may include components or known components that may be included in a model of the screw 150. The model of the screw 150 may include a CAD model or other computer or digital model of the screw 150. The model of the member, such as the screw 150, may be used to generate a simulated image or representation, as illustrated in FIG. 3A and FIG. 3B. The representation 200 may be generated based upon techniques to simulate an image acquired of the screw 150 with a selected imaging technique. For example, the representation 200 may be generated based upon the known components of the model of the screw 150 and how the components would interact with an x-ray imaging system to generate the representation 200. Various x-ray simulations techniques such as those using Monte-Carlo techniques may be used to calculate x-ray interactions and attenuations with selected materials. Various interactions may include X-ray scatter and beam hardening, and others understood by one skilled in the art. The x-ray interaction techniques may be used to generate the representation 200 of the screw 150.

According to various embodiments, the shaft 154 of the screw 150 may be formed of a first material and may be illustrated or used to generate a shaft representation 204. The head 160 may be formed of a different material, as discussed above, and the known interactions may be used to generate the head representation 208. It is understood by one skilled in the art, however, that the head and shaft may be formed of the same material and may be both represented in a same or similar manner in the generated image.

The representation 200 may include both the shaft representation 204 and the head representation 208 along with the geometry and configurations of the shaft 204 and the head 208 relative to one another. It is understood, however, as discussed above, that the representation 200 may also include various geometries such as an illustration or representation of a trough 212 which is the representation of the trough 168 of the screw 150 discussed above. Further, as discussed above, the shaft 154 may include one or more apertures, also known as holes or fenestrations, 158 and may also be represented as a fenestration 214 in the representation 200. The trough representation 212 may be illustrated at a selected geometry relative to the fenestration representation 214 in the screw representation 200 in FIG. 3A.

In various embodiments, the screw 150 may be orientated differently than that illustrated in FIG. 3A, as illustrated in FIG. 3B, including orientation of the head relative to the shaft 154. For example, the trough representation 212 of the head representation 218 may be rotated or angled relative to the shaft representation 204, as illustrated in FIG. 3B. As illustrated in FIG. 3B, the trough representation 212 may be rotated relative to the shaft representation 204 such that the hole 214 is not viewable when viewing along the trough 212. Thus, it is understood, that the model of the screw 150 may be manipulated to alter the position of the head 160 relative to the shaft 154 and thus generate representations that differ from one another, such as the first representation 200 (FIG. 3A) or the second representation 230 (FIG. 3B).

It is further understood, however, that the representations 200, 230 are merely exemplary. The representations of the screw 150 may also be generated with the model and various imaging technique modeling methods, as is generally understood in the art. The geometry of the screw 150, such as the length 172 of the shaft 154, the width of the shaft 176, and other dimensions may also be altered in the model of the screw 150. Altering these dimensions may alter representations of the screw 150 when generating images based thereon. Accordingly, the screw representations 200, 230 are merely exemplary for the current discussion.

Nevertheless, the representations 200, 230 of the screw 150 may be used to simulate an imaging technique, such as an x-ray image acquisition, of the screw 150. Based upon the CAD models of the screw 150 the representations 200, 230 may be understood to be substantially ideal representations of the screw 150 based upon the imaging technique. Thus, the representations 200, 230 may be used to train an artificial neural network (ANN), as discussed above and further herein to identify (e.g. segment) the screw 150 in an image.

A training image may be incorporated into a training data set, where a training data set may include a plurality of training images. To generate a training image, according to various embodiments, a representation may be labeled in an image or an entire image may be labeled. A labeled image may be an image that is identified to include a selected member (e.g. a screw) or a pre-segmented portion of the training labeled image. The labeled image is used to train or allow the ANN to train and learn selected parameters, such as weights and biases and/or other parameter features to identify elements or portions within the image. In certain instances, however, such as positioning implants in a subject, acquiring or labeling a training data set may be obtained by generating images with the representations 200, 230, or appropriate representations as discussed above.

Figure 4:
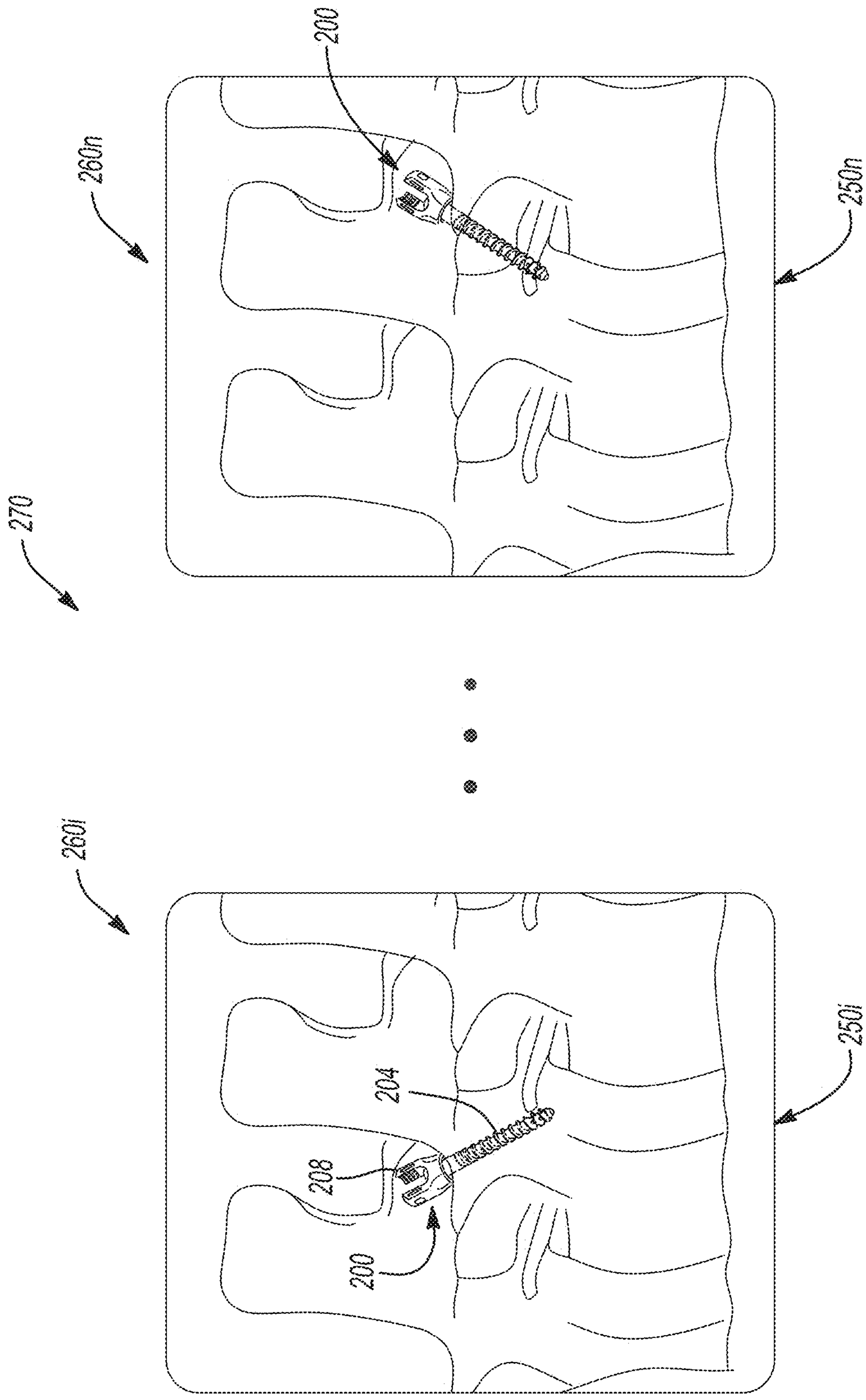
FIG. 4 is a simulated illustration of generating a simulated training image for generating a training data set, according to various embodiments.

With reference to FIG. 4 a pre-acquired image of a subject, such as an image of a cadaver, an image of an unknown human subject, or the like, may be used as a pre-acquired image 250. The pre-acquired image 250 may have overlaid thereon or superimposed therein the representation 200 of the screw 150. The representation 200 may include the various portions, as discussed above, including the head representation 208 and the shaft representation 204. These representations may be overlaid on the pre-acquired image 250. The pre-acquired image 250 with the representation 200 overlaid thereon may then be used as a training image 260. As discussed above, a plurality of the pre-acquired images 250 may include one or more of the representations 200, and/or the representation 230, or other appropriate representations, to form a training data set. It is understood that the pre-acquired image 250 may have overlayed thereon a plurality of the representations at different locations, different orientations, and at different depths.

Each different overlaid position and or position of the representations 200, 230 of the member may be used as a different training set. Thus, a plurality of the pre-acquired images may be saved as a training data set 270 having a selected number of training images 260*n* having a selected number of pre-acquired images 250*n* with the representations, such as the representation 200, overlaid therein. The training data set 270 may then be used to train the ANN, as discussed further herein. The training data set 270 may be labeled, each of the training images 260 to 260*n* are identified as including the screw 150, such as by representation with the representation 200. Further, the specific identity and location of the screw 200 is known in each of the representations, based upon the predetermined and known placement of the representation 200.

The training data set 270 may include various qualities. For example, a user (e.g. an expert including a surgeon) may position the representation 200 and/or grade positions of the representation 200 for selected procedures. For example, the training image 260 may be used to place the representation 200 of the screw 150 at a selected location for performing or augmenting a spinal fusion. The screw 150 may be positioned in a plurality of locations and in more than one vertebrae to allow for positioning of a rod there between. Therefore, the surgeon may grade the training image 260 based upon the locations of the representation 200 based upon a location of the screw 150. Further, in various embodiments, the expert (e.g. the user 36) may place the representation 200 in an ideal location for a selected procedure. Thus, the training image 260 and the training dataset based thereon may include not only labeled images for identifying the representation 200 of the screw 150 but also information related to a grade or ideal location of the screw 150 for a selected procedure.

Figure 5A:
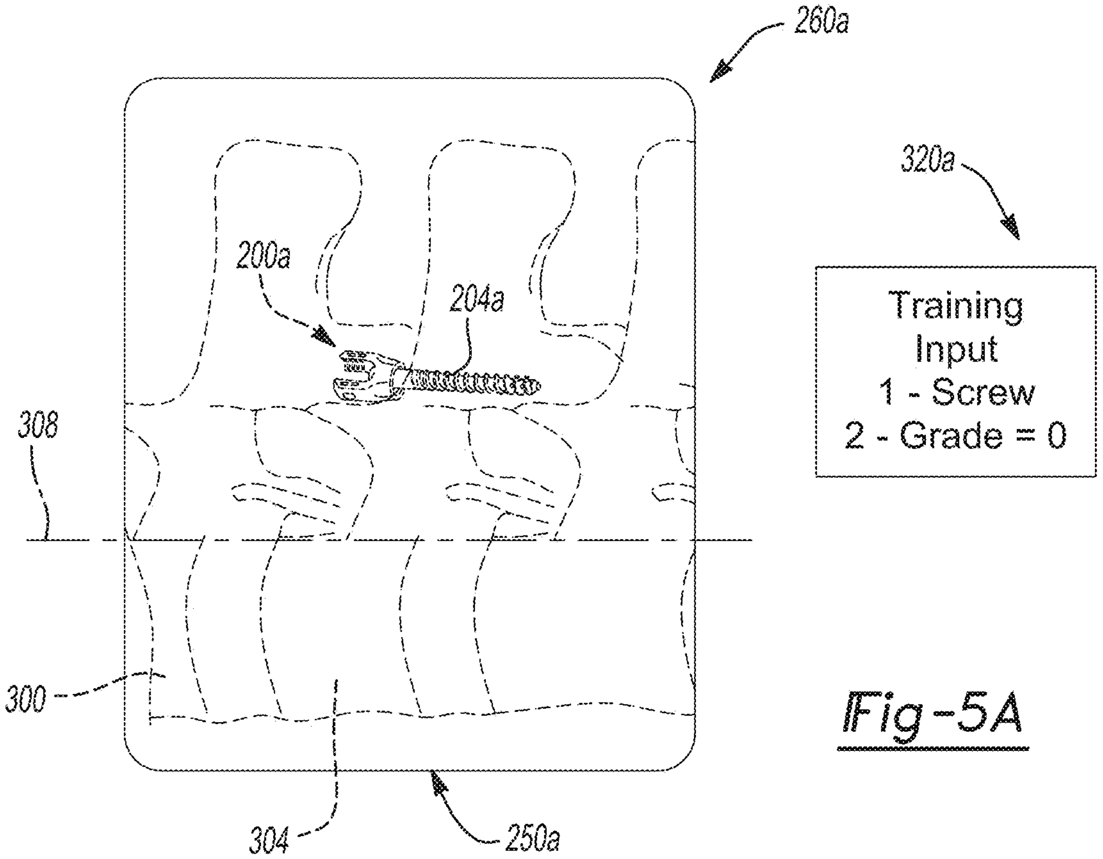
FIG. 5A and FIG. 5B are alternative views of simulated training images.
Figure 5B:
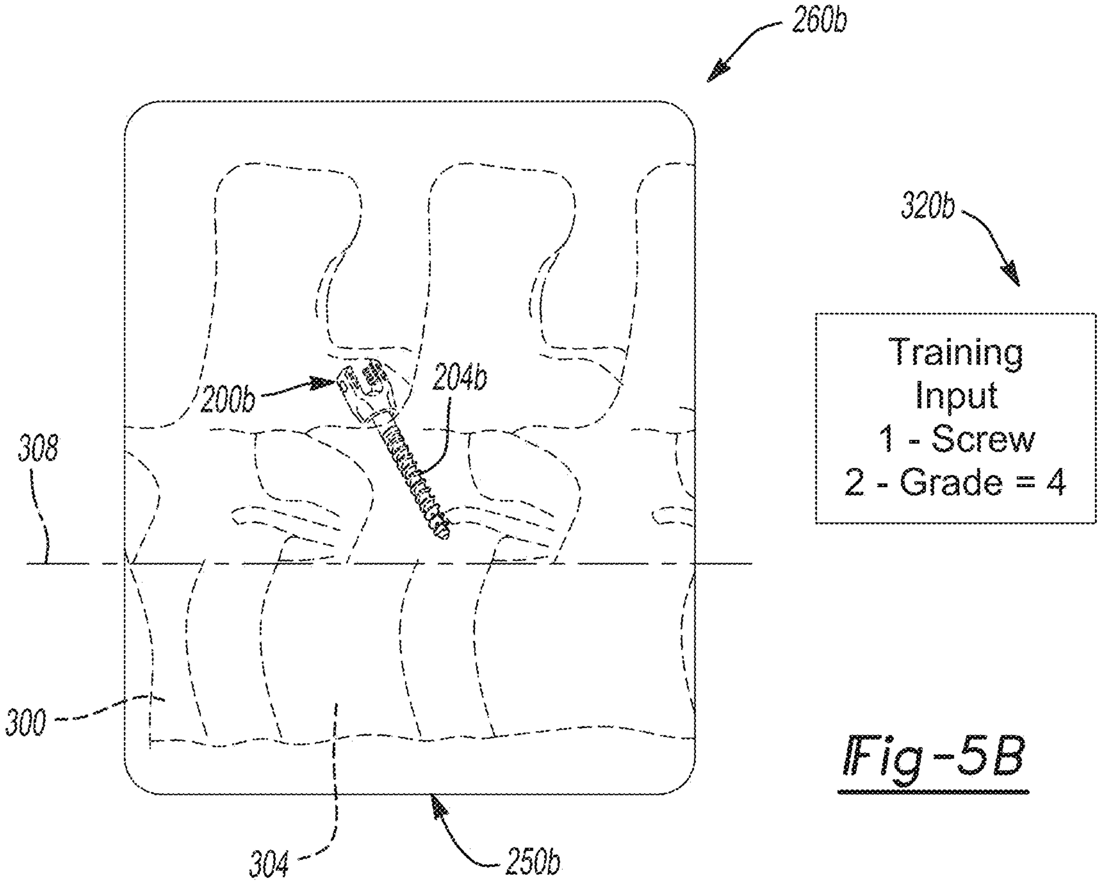

With continuing reference to FIG. 4 and additional reference to FIG. 5A and FIG. 5B various examples of the training images in the training dataset are illustrated including a training image 260*a* and a training image 260*b* are illustrated, respectively. As illustrated in FIG. 5A, the training image 260*a* includes a pre-acquired image 250*a* that illustrates a first vertebrae 300 and a second vertebrae 304. A first representation 200*a* of the screw 150 is illustrated positioned in the second vertebrae 304. The representation 200*a* may illustrate the screw 150 positioned substantially axially along an axis 308 of the vertebrae 300, 304. Thus, the shaft representation 204*a* may be positioned substantially on the axis 308.

If the image is graded or analyzed by the user 36 before use as a training image, the user may identify the representation 200*a* in the training image 260*a* and further provide a grade, such as at a rating scale between 0 and 5, where 0 is unlikely to provide a positive result and 5 is highly likely to provide a positive result. The user 36 may provide an input 320*a* upon reviewing the training image 260*a* and the training image 260*a* may be included in the training set 270 and the input 320*a* may be included with the training image 260*a*. Accordingly, the training data set 270 may include both the training image 260*a* and the training expert input 320*a*.

In a similar manner, the training image 260*b* may include a pre-acquired image 350*b* that may include the image of the two vertebrae 300, 304 with a representation 200*b* of the screw 150 positioned within the second vertebrae 304. The representation 200*b* may include the shaft 204*b* that is positioned with a substantial angle relative to the axis 308. The location (e.g. the position and the orientation) of the representation of the member 200 in the image 250, may be altered relative to a first or previous training image 260*a*.

In further training images, including the training image 260*b*, the user 36 may view the training image 260*b* including representation 200*b* and provide training input for the training image 260*b* such as a training input 320*b*. Again, the user 36 may identify that the training image 260*b* includes the representation 200*b* of the screw 150 and provide a grade regarding the position of the screw, again on the same scale as discussed above. Thereafter, the training data set 270 may then include the training image 260*b* and the related training input 320*b*.

The training data set 270, discussed above, may then include both the training image 260*a* and the training input 320*a* related thereto and the training image 260*b* and the training input 320*bm*, or any appropriate or selected number of training images and training grades (if selected). Thus, the training data set 270 may include both labeled images, such as the training image 260*a* and 260*b* and further related data, such as a grading thereof. As discussed further herein, therefore, the ANN may be trained to determine or identify images for various purposes, such as both to segment selected features, such as the screw 150 based upon the training representations 200 and the training images 260, and also assist in identifying or grading a position or planned position of the representation based upon the training inputs 320 associated with the respective training images.

Figure 6:
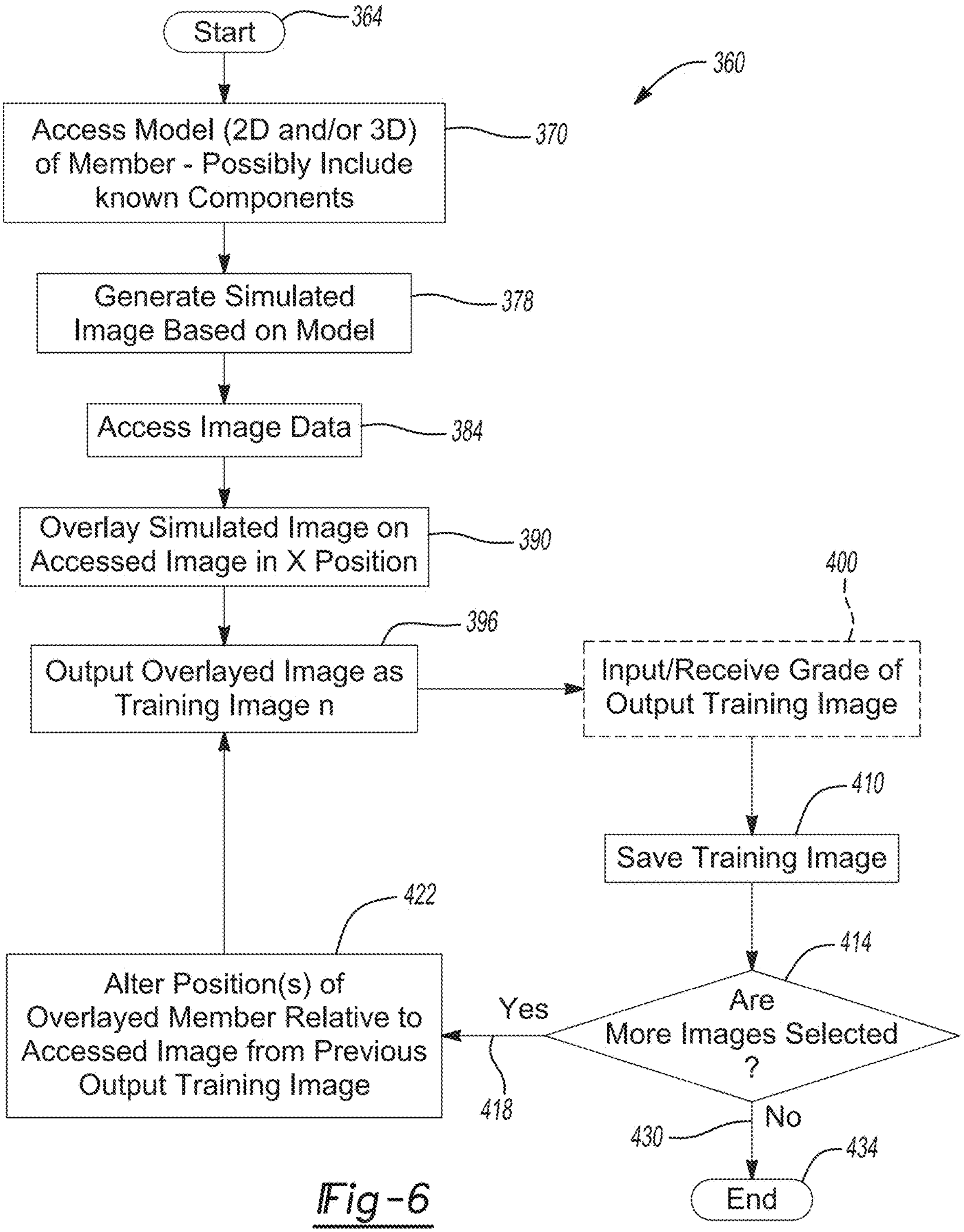
FIG. 6 is a flow chart illustrating a method to generate a training data set, according to various embodiments.

The training data set 270, as discussed above, may include the generation of a plurality of training images, as illustrated in FIG. 5A and FIG. 5B. The one or more training images may be saved in a selected memory for access at a selected time for training the ANN. The training data set 270 may include the generated training images 260 and/or the grading 320, as discussed above. In various embodiments, a process for generating and storing the training images may be incorporated into process as illustrated in a flowchart 360, as illustrated in FIG. 6.

The process 360 begins at start block 364 including accessing a model of a member which may be made in block 370. IN various embodiments, the model may be a two-dimensional model (2D) and/or a three-dimensional (3D) model of the member. Further, a plurality of views of the member in a plurality of 2D model images may be accessed and/or created. Similarly, the 3D model may be rotated to generate a plurality of views. Thus, accessing a 3D model, discussed herein, is intended for the present discussion not to limit the disclosure herein.

The model may include various parameters of a member may be known and accessed. As discussed above, the model of the screw 150 may be included in a computer aided drafting (CAD) model that includes various geometries, sizes, features, and the like, as discussed above. For example, lengths, diameters, angles, and the like may be included in the model of a member. It is further understood that the member may be any appropriate member, and the discussion of the screw 150 herein is merely exemplary.

Further the 3D model may include various parameters for portions and materials and/or portions of the model. Again, as discussed above, the screw 150 may include various parts or movable members such as the shank 154 and the head 160. The shank 154 may be formed of different materials than the head 160, as discussed above. In various imaging modalities, such as x-ray imaging, the different materials may interact with the x-rays in different ways to generate specific imaging or detection on a detector grid or film. The interaction of the different materials with the x-rays may be saved or determined as known or predetermined interactions with the materials. The 3D model may therefore, incorporate the known interactions with the x-rays, or any appropriate imaging modality, including with individual portions of the member. The interactions may be determined based upon x-ray beam spectrum, component material, and detector sensitivity, as is generally known in the art.

The model of the member, therefore, may be used to generate one or more simulated images based upon the model in block 378. Generating a simulated image in block 378 may include simulating the projection of x-rays through the model and simulating a detected image based thereon. In various embodiments as discussed herein, the simulated images may include projections through the model, such as if the model is a 3D model. The simulated images may be 2D images based on a projection through the 3D model. Alternatively, or in addition thereto, the generated images may be 2D images based on the model when the model is a 2D model.

The simulated image, in various embodiments, based upon the 3D model including various portions, such as the known features, may be generated in any appropriate manner, such as applying the known interactions of the x-rays with the geometry and dimensions saved or incorporated into the 3D model from block 370, to generate the simulated image in block 378. Generally generating a simulated image in block 378, therefore, incorporates the accessed 3D model from block 370 and a predetermined or known interaction of an imaging modality, such as x-rays, with the materials of the member and/or the geometry of the member in the 3D model.

The simulated images of the member generated in block 370 may include a single image and/or a plurality of images at different orientations, angular positions, or the like of the generated simulated image. The generated image or images may be 3D or 2D. With a single three-dimensional simulated image, the three-dimensional simulated image may have its position and orientation altered between various training images. In the alternative, or in addition thereto, a plurality of simulated images may be made in block 378 and each different simulated image may be overlaid on one or more acquired images such that the generated image is individually placed and/or multiply placed in accessed images, as discussed further herein. Similarly, a plurality of 2D images may be generated that simulate different orientations and locations of the member in space.

Image data or images may be accessed in block 384. The accessed images from block 384 and the generated simulated image from block 378 may be used to overlay a simulated image on the accessed image in a position (e.g. a first position or first known position "n") in block 390. The overlaying of the simulated image on the accessed image may include overlaying the representation 200*b* on the accessed or patient image 250*b*, as illustrated in FIG. 5B. The generated simulated image may be overlaid in a single location or position, including three-dimensional location and orientation (e.g. including at least three degrees of freedom of orientation) relative to the accessed image. In various embodiments, as discussed above, this may include positioning the generated image or a representation of the screw 150 relative to a vertebrae, such as the second vertebrae 204*b* in an accessed image 250*b*, as illustrated in FIG. 5B.

After overlaying the simulated image on an accessed image in block 390, outputting the overlaid image as a (e.g. first) training image in block 396 is performed. Outputting the overlaid image as a training image may include the training image 260*b* and/or 260*a*, as discussed above. As further discussed above, and discussed further herein, a plurality of training images may be made. Accordingly, the training image output in block 396 may include the image 260*a*, illustrated in FIG. 5A, or the image 260*b*, as illustrated in FIG. 5B. Regardless, the outputted overlaid image may be a training image as discussed above.

The output training image may optionally include grading data or information, as discussed above. Accordingly, an input of a grade with an output training image in block 400 may optionally be performed. The input of a grade may be based upon the observation of the user 36, as discussed above, of the overlaid position of the generated image relative to the accessed image that is output in block 396. The user 36 may grade the position of the overlaid generated image and may input the grade or input a grade that is then related to the specific output training image. The input grade may be received in block 400.

The output overlaid training image may then be saved in block 410. If the optional input grading is performed, the input grading may also be saved with a specific image in block 410. Thus, the training data set 270 may be initialized or started by the output overlaid first image that may optionally include a grading, that is stored for later access.

After saving in block 410 of the training image from block 396, with or without the grade input from block 400, a determination block of whether more training images are selected in block 414 is made. The determination of whether additional or more training images are selected may be based upon a selected number of training images to train the ANN. The number of images for the training data set may be based on an accuracy selected for the ANN in determining or segmenting a feature in an image, a speed for segmentation, or other appropriate parameters.

Nevertheless, if additional images are selected, a YES path 418 may be followed to alter the position of the overlaid member relative to the accessed image from a previous output training image in block 422 is made. As discussed above, altering the position of the overlaid member may include positioning the overlaid member in a different position and/or orientation relative to the vertebrae, such as the second vertebrae 204*a*, 204*b*, changing a geometry of the member at a previously selected position or orientation, (e.g. changing an orientation of the head representation relative to the shaft representation, positioning a different size member, or the like). Further, altering the position of the overlaid member may include selecting a different location and/or orientation, such as the first vertebrae 300, as discussed above, selecting a different part of an anatomy or other portion of the selected image, or the like. Further, a general trained model may be trained on multiple members with multiple portions of a subject, such as a human subject, and therefore selecting a different accessed 3D model (i.e. different member from the screw 150) may be selected for altering the overlaid position of the member such as selecting a femoral implant, tibial implant, or the like.

After altering the position of the overlaid member in block 422, an output of an overlaid training image in block 396 may occur, similar to that discussed above. The output image may be graded in block 400, if selected. The output image may then be saved as a training image in block 410, as also discussed above. Accordingly, the method 360 may generate a plurality or selected number of training images for a training data set, such as the training data set 270 discussed above, by altering the position of the overlaid member to a different position from a previous position in block 422 re-outputting the overlaid image in block 396 and saving the image in block 410. It is understood, therefore, that a plurality of training images may be saved in block 410 to an appropriate memory medium, such as a solid state memory, magnetic medium, or other appropriate memory system. The saved image may be accessed locally and/or over a selected network, either wired or wireless, according to selected and known protocols.

After saving the image in block 410, the determination or decision block 414 of whether more training images are selected may be entered. If an appropriate number of training images has been saved in block 410, a NO path 430 may be followed to end the training data set generation method 360 in block 434. Accordingly, the training image data set generation method 360 may be used to generate one or a plurality of images for training a selected system, such as the ANN. The training image data set method 360 may be used to generate an appropriate number of images to generate the training data set 270, discussed above, that may be used to train the ANN to identify and/or segment selected features, such as an implant member including a pedicle screw 150 imaged therein.

The method 360 may be included in executable instructions that are executed by a selected processor and/or instructions that are incorporated into an application specific processor or integrated circuit, as is understood in the art. However, the method 360 may be used to efficiently and effectively generate a plurality of training images for training a selected ANN, such as a convolutional neural network (CNN) to assist in segmenting or identifying features in a later acquired or accessed image, as discussed further herein. Accordingly, the method 360 may be included in an algorithm as instructions that are executed by a processor that accesses image data, overlays a generated simulated image of an item based upon a 3D model on the accessed image, and then saves the image as a training image in block 410. The algorithm may be iterated to create a plurality of the training images with the training dataset.

Accordingly, the method 360 may be executed to generate a plurality of images without requiring an actual image of a subject being acquired. An actual image of a subject may include a subject with a selected member (e.g. the screw 150) that is labeled. The method 360 may be used to eliminate such a manual identification and labeling of an image by generating the training image based upon a known 3D model of the member and overlaying it on an accessed image to generate the training image and then altering the overlaid member for generating a plurality of training images.

Once the training images are generated according to the method 360, the training data set 270 may be used to train the ANN, as discussed further herein. The trained neural network or the machine learning process may be used to assist in identifying a selected member, such as the member used in the training data set, to assist in identifying and/or segmenting members in a later acquired image.

Figure 7:
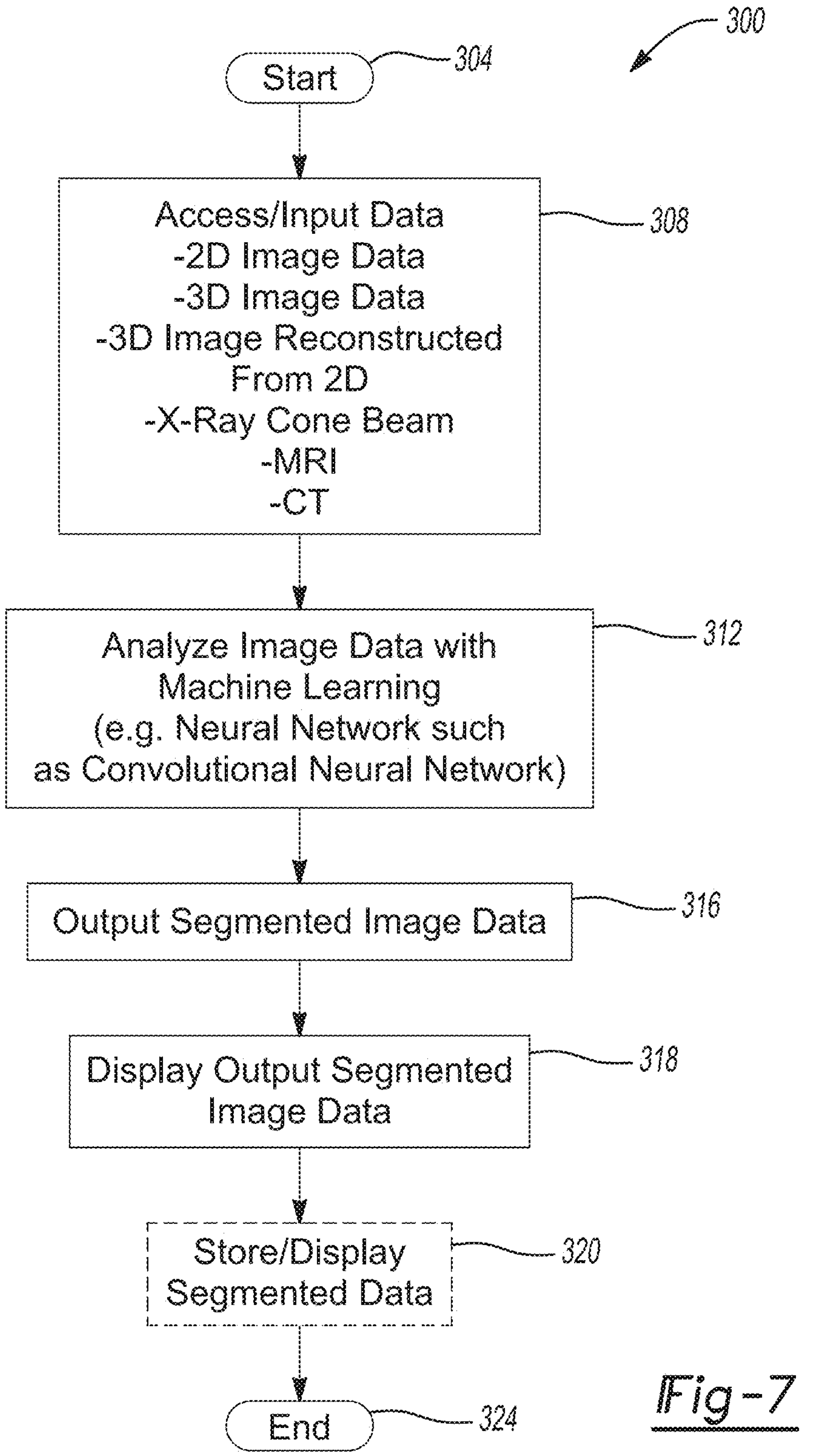
FIG. 7 is a flow chart of an exemplary use of a trained artificial neural network for segmentation.

The trained ANN may be used to segment a portion of an image that is acquired after the training, as discussed above. For example, with reference to FIG. 7, a process or method for identifying a portion of an image, also referred to as segmenting an image, is illustrated in the flowchart 300. The flowchart 300, is a general flowchart and a more specific process, such as a CNN, will be discussed in further detail herein. Generally, however, the segmentation process begins with an input of image data, such as the image data used to generate the image 30 on the display 32. The image data may include any appropriate image data such as computed tomography image data, magnetic resonance image data, X-ray cone beam image data. Further, the image data may be generated with any appropriate imager such as the O-arm® imaging system, as discussed herein. The O-arm® imaging system may be configured to acquire image data for a 360 degrees around a subject and include 2D image data and/or a 3D reconstruction based on the 2D image data. Further, the O-arm® imaging system may generate images with a x-ray cone beam.

The process 300 may start in block 304. The process 300 may then include accessing or retrieving or acquiring image data in block 308. The image data may include 2D image data or a 3D model reconstructed from the 2D image data in block 308. The 2D image data or the reconstructed 3D image data may be from an imaging system such as the imaging system 20. The imaging system 20, as discussed above, may include the O-arm® imaging system. The imaging system 20 may generate a plurality of two dimensional image data that may be used to reconstruct a three dimensional model of the subject 28 including one or more of the vertebrae 28*v*. The acquired image data in block 308 may also be acquired at any appropriate time such as during a diagnostic or planning phase rather than in an operating theatre, as specifically illustrated in FIG. 1. In various embodiments, the image data accessed in block 308 may include image data during a procedure, such as after placement or implantation of the screw 150. The image data acquired or accessed in block 308 may, therefore, include image data of the screw 150 positioned within the subject 28.

The image data acquired with the imaging system 20 may be of a selected image quality that may be difficult to identify various boundaries of image portions, such as the vertebrae 28*v*. The image data may also be used for viewing a location and orientation of the screw 150, when in the image data. Thus, as discussed further herein, a neural network may be used to automatically identify the boundaries of the imaged portions, such as the screw 150, to segment the image data.

The image data from block 308 may be processed or analyzed with a machine learning system or process, such as the ANN, in block 312. The artificial neural network (ANN) may be a selected appropriate type of ANN such as a convolutional neural network (CNN). The CNN may be taught or learn to analyze the input image data from block 308 to segment selected portions of the image data. For example, as discussed above, the CNN in block 312 may be used to identify boundaries of members, such as implanted members including the screw 150. As discussed above, the boundaries may be determined and illustrated, such as displayed on the display device 32 either alone and/or in combination with the image 30.

Accordingly, analyzed image data may be output as segmented image data in block 316. The output segmented data from block 316 may be displayed with the display device 32 in block 318, stored in block 320, or otherwise, in addition to or alternatively to the above, further analyzed or processed. The output segmented data may be stored in a selected memory system in block 320, such as the navigation memory 88 or the image memory 192 (See FIG. 1). The output segmented image data may segment selected portions, such as the screw 150 as discussed above, for various purposes. The process 300 may, in various embodiments, end in block Accordingly, the flowchart 300 can start in block 304 and then access or input image data in block 308 to output segmented image data (and/or segmented masks) in block 316 and display the segmentation in block 318 and/or store the segmented image data in block 320. The process 300 may then end in block 324 and/or allow for further processing or workflow, as discussed further herein. It is understood that the selected portions of the flowchart or process 300, however, may include a plurality of additional steps in addition to those discussed above. For example, the CNN may be developed and then taught to allow for an efficient and/or fast segmentation of a selected portion of the image data that is accessed or inputted from block 308. The segmentation may be a specific, such as identifying the vertebrae, or general such as identifying selected boundaries or changing contrast in the image data.

A CNN that may be used to analyze the accessed image data in block 312 may be developed and taught, as briefly discussed above, and discussed in further detail herein. The CNN is based upon generally known convolutional neural network techniques such as that disclosed in Özgün çiçek, Ahmed Abdulkadir, Soeren S. Lienkamp, Thomas Brox, Olaf Ronneberger, "3D U-Net: Learning Dense Volumetric Segmentation from Sparse Annotation", International Conference on Medical Image Computing and Computer-Assisted Intervention, Springer, Cham, pp. 424-432 (2016) (https://arxiv.org/pdf/1606.06650.pdf (2016)), incorporated herein by reference. The CNN may be developed to efficiently identify selected portions of images by analyzing the image data and causing an excitation of an artificial neuron. The excitation of a neuron in the CNN may be based upon determined and "learned" weights and various parameters. The excitation, therefore, may simulate a judgment or calculation of a selected learned portion in a new input, such as the image data accessed in block 308. According, the input image data from block 308 may be analyzed or processed with the CNN in block 312 based upon a teaching of the CNN, as discussed further herein, with the training data set 270.

In various embodiments, as is understood by one generally skilled in the art, the CNN generally allows for the teaching of the CNN to identify image features in image data, such as the accessed image data in block 308. For example, a kernel (also referred to as a filter) of a selected dimension (e.g. 3×3 pixels) that may be previously defined and/or learned by the CNN. The filter may then be applied to the accessed image in the accessed image data 308 in a stepwise manner, such as moving the filter one pixel or one voxel at a time. The filter is a single component or parameter in the CNN which may consists of hundreds or thousands of interconnected filters arranged in layers. The first layer filters operate on the image, filters on the next layers operate on the output of the previous layers. That is, the filter of a selected size may be moved stepwise a selected dimension, such as one pixel or voxel, throughout the entire image. The filter may be learned and used to identify a selected portion or an "interesting" portion of the image.

In various embodiments, the filter (K) is applied to an image (for example a two dimensional image). A product, or summation of products (such as a dot product of the filter K and portion of the image I) may then be saved or stored for a further layer as a convolutional product matrix I*K. The product matrix, will have a dimensions less than the input given the size of the filter and the stride (amount of movement of the filter in the image I) selected. The summation in a two dimensional manner is illustrated or defined by equation 1 (Eq.1):

$$(I*K)_{xy} = \sum_{i=1}^{h}\sum_{j=1}^{w} K_{ij} \cdot I_{x+i-1,y+j-1} \quad \text{Eq. 1}$$

Eq. 1 includes the image data I (i.e. includes pixels or voxels) in a selected array. K represents the kernel or filter where the filter has a height and width (i.e. in a two dimensional kernel relating to two dimensional image data) and the output I*K of convolutional matrix is the summation dot product of the input image I and the kernel K according to Eq. 1.

The CNN includes a convolution that includes moving the filter over the input image to generate an activation map, of which the I*K is a part. An activation map layer is formed by the application of each filter and layer of filters to the image. A plurality of the filters, which may be learned by the CNN, may then be stacked to produce the output volume (e.g. for three dimensional image data) that generates a segmentation of the input image data. Thus, the CNN may output a three-dimensional (3D) output image or model that includes or is a segmentation of the image data.

Various features may be incorporated into the CNN, including those as known in the art and/or additional features to assist in determining and creating an efficient segmentation of a selected image. For example, an amount of connectivity may include a local connectivity that is equivalent to the selected filter size. It is understood that filter size may be selected based upon a resolution of an input image, a processing speed selected, or the like. In various embodiments, the filter size may be selected to be about 3×3×3 in size, such as pixel dimensions. It is understood, however, that different kernel sizes may be selected.

A size of an output may also be dependent upon various parameters that are selected to choose or select an output volume. For example, various parameters may include depth, stride, and a zero-padding or any appropriate padding. Depth includes a number of distinct different filter that are convolved in a layer. For example, the filter includes a selected array of convolution operations (i.e. an array of ones and zeros). It is understood that a plurality of different filters may be applied to each layer in a CNN where the filter includes different operational arrays. A stride refers to the number of elements (e.g. pixels, voxels, or other selected image element) that determine the amount of movement of the filter within the input volume per step. Padding may further be added to an input image in any particular layer to account for the decrease in an output image side due to the striding of a kernel within an image. For example, moving the filter with a stride equal to one pixel will decrease the output matrix by two pixel dimension (e.g. an input of 7×7 having a kernel 3×3 with a stride of 1 will output a matrix of 5×5). Padding the input to include zero image data or pixels can maintain the output size to be equal to the input size of the volume or image.

In the CNN, in addition to the convolution including the size of the filter and features of the filter, as discussed above, additional operations may also occur. For example, in the CNN a pooling layer may be added to down sample the output. For example a pooling, such as a max-pooling, operation may attempt to reduce the number of parameters and reduce or control over fitting. The max pooling may identify or select only the maximum volume (e.g. a maximum pixel or voxel value) within a filter size for an output. For example, a max pooling filter may include a 2×2 filter that is applied in a stride of two along a selected dimension, such as two dimensional image for a two dimensional image. The max pooling will take only the maximum valued pixel from the filter area to the output.

Additional operations may also include batch normalization such as that described in Sergey Ioffe, Christian Szegedy, "Batch Normalization: Accelerating Deep Network Training by Reducing Internal Covariate Shift", ICML, 2015 (https://arxiv.org/abs/1502.03167 (2015)), incorporated herein by reference. The batch normalization may be applied at selected points or layers in the CNN, such as an initial layer or after each convolutional layer. The batch normalization may cause or will cause an activation throughout the CNN to achieve a selected distribution, such as a unit Gaussian distribution, at a selected point in the training, such as a beginning point in the training. Batch normalization allows increased depth of the network, accelerated training, and robustness to initialization.

The ANN (such as the CNN) may include one or more neurons in the network. An output from a neuron in a layer may include calculating a weighted sum and adding a bias to an activation function is then applied to the input and bias to produce an output. The weights from a neuron or layer output may be further analyzed or incorporated into the CNN. The output from neurons, to achieve the selected output, may have a weighted loss function to assist in activating or reducing an influence of a selected activation function of a neuron. A weighted loss function gives different importance to different labels based on certain properties, e.g. boundary of an object vs non-boundary. The labels may be features identified in the image and/or included in the filters.

An output from a neuron includes an activation function, as generally understood in the art. One skilled in the art will understand that various activation functions for selected neurons may be employed. A rectified linear units function is a function generally defined as f(x)=max(0,x). Accordingly, the rectified linear units function can provide an activation of a neuron in the CNN when the rectified linear unit activation function is greater than a selected threshold. In the rectified function only a positive component of the function is compared to the threshold. In an output layer, the mask or delineation of a selected portion of the input image identified as a selected object (also referred to as a label, e.g. a vertebra or portion thereof) is determined if the output probability map is above a selected threshold probability, such as 35%. In various embodiments, the mask or delineation of the portion of the input image identified as a selected object is the label with the highest probability as opposed to a selected threshold or only a selected threshold.

The filter, in a three dimensional image, may include a height, width, and depth. The filter may, however, also include a 2D image that includes only two dimensions, such as height and width. During training of the CNN and use of the CNN, the filter may then be passed over or compared to image data, such as used to generate the image 30 (which may be displayed on a display device 32 or note) to determine if a neuron is activated and generate an activation or feature map based upon the presence or lack thereof of an activation, as described above. The filter may be determined or formulated to activate based upon a selected feature, such an edge or other identified portion. The CNN may include various known layers of the CNN for segmentation, as is generally known in the art. The CNN, therefore, may include convolution layers, down sampling layers, deconvolution layers, etc. The deconvolution layers may be applied to up sample a final segmentation map at the resolution of the original image. In various embodiments, the deconvolution layers may densify a sparse activation. The deconvolution layer may also be referred to as a transposed convolution as described in A guide to convolution arithmetic for deep learning, V Dumoulin, F Visin-arXiv preprint arXiv: 1603.07285, arxiv.org (2016), incorporated herein by reference.

As is understood by one skilled in the art, training of the CNN with the training data set 270 may include various specific features such as resampling the training data by including each image therein, to a selected size, resampling a selected voxel size, adding a selected amount of padding, or other features. Generally, during training, normalization of image data and application or training of the CNN with the normalized data is then used. The CNN may be trained with the training data set 270 to generate a plurality of weights and biases in each neuron of the CNN to perform a task, such as segmentation of the screw 150, in a later acquired image. Training the CNN, or any appropriate ANN, may then be performed with the training data set to assist in identifying and segmenting a screw (or other appropriate member) in a later accessed data.

After training the CNN, the trained CNN may be used to segment a later accessed or acquired image based upon the determined weights and biases in the CNN. For example, with reference to FIG. 8, an exemplary schematic diagram of an application of a CNN to an image is illustrated. As discussed above, with relation to the process 300, the image 32 may be the accessed image in block 308. The CNN may then be applied to the image to analyze the image with the CNN in the analysis block 312. As discussed above, the CNN may include one or more filters that are applied to an image to generate a feature or activation map 340. The CNN may include the application of one or more filters to an image and the feature map may include one or maps based upon the filter that have identified various features within the input image 32.

In a plurality of layers of a CNN, as is understood in the art, various additional filters and/or neuron weights and biases may be determined during training and calculated to determine whether neurons are activated to generate a sub-sampling data set 350 and finally a full connection or analysis connection 360. The CNN, therefore, as executed or described in block 312, can include various features to segment the image 32 based upon the trained CNN. As discussed above, the training data set 270 is used to train the CNN to assist in identifying or segmenting the member, such as the screw 150 from the training data set.

Based upon the trained CNN, the screw 150 may be segmented within the image 32, if present, and may include a screw projection 150*i* and 150*ii*. In various embodiments, such as if the image includes an image of the subject with two screws placed in the subject, may segment two screws based on the application and analysis of the CNN in block 312 to generate the output 316. As discussed above, the output may include segmented screws such as 150*s* and 150*ss*. The segmentation of the screw 150 in the image, including the segmentation 150*s* and 150*ss* is based upon the trained CNN. Accordingly, activation of the neurons in the trained CNN allow for identification of various boundaries and portions of the screw 150 that are within the image 32 as the image of screws 150*i*, 150*ii*. The training of the CNN based upon the training data set 270, as discussed above, is based upon the generation of a plurality of images with a simulated image that is generated of the screw based upon the CAD model that may include various features such as the known components.

The output 316, which may include the segmented screws 150*s* and 150*ss*, may be stored for later use and analysis and/or displayed on the display 32, such as the display 32 as illustrated in FIG. 1. Thus, the user 36 may view the segmented screws that are segmented by the CNN in the process 312. The user 36 may refine the segmentation of the screws after the initial or CNN segmentation, such as with a later or refined manual segmentation, if selected. It is understood, however, that the user 36 may view the initial segmentation with or without manual refinement and/or may understand the position of the screws based upon the automatic segmentation with the analysis of the image in block 312.

Figure 8:
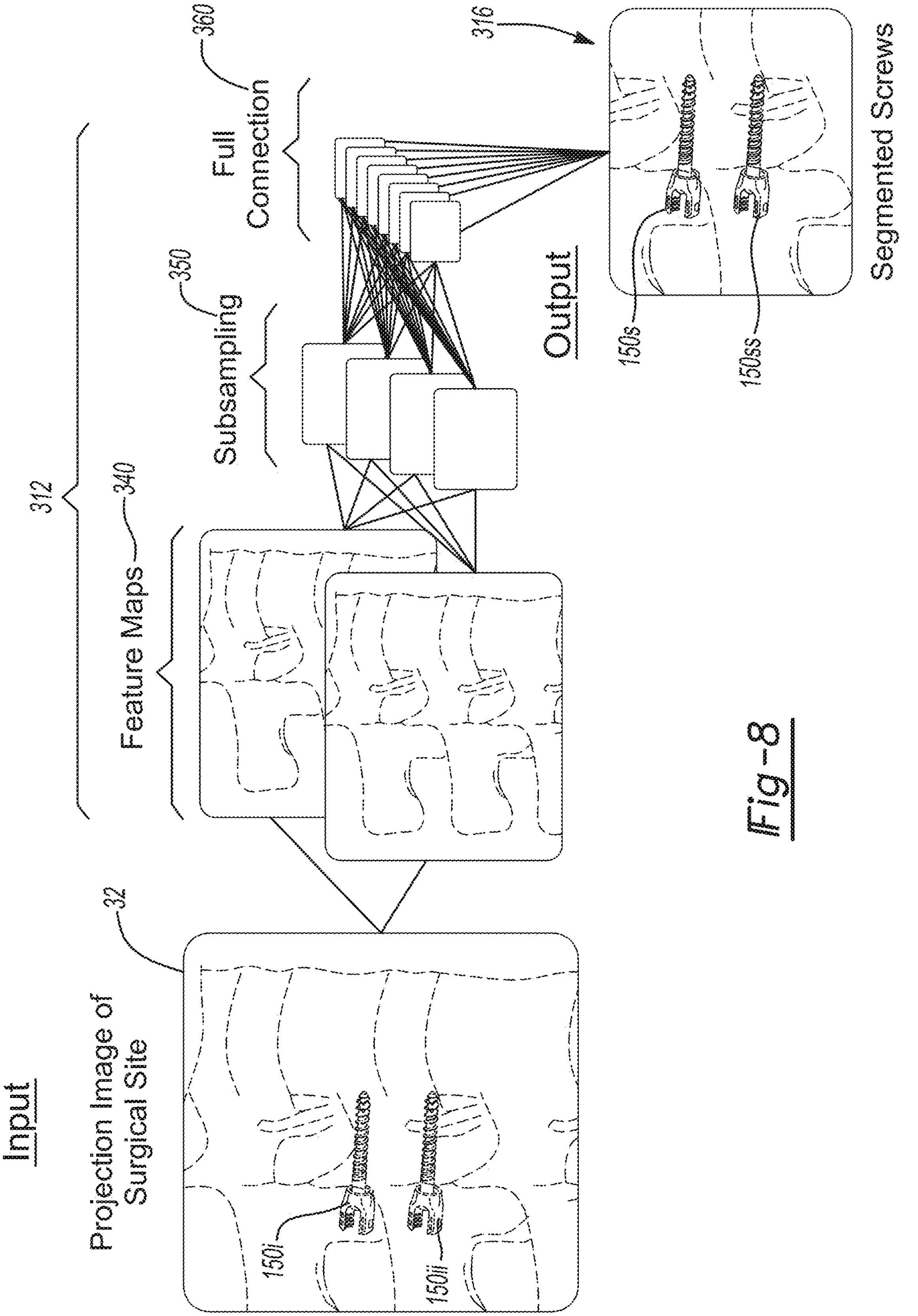
FIG. 8 is a visual illustration of a trained artificial neural network for segmentation.

The automatic segmentation of the screws from the image 32 allow for the user to efficiently understand the position of the screws without manual segmentation of the screws from the image 32. Further, the user 36 may view the automatic segmentation to assist in determining an efficiency or completion of the procedure and/or determining a following or further step. Nevertheless, the process 300 may be used to segment the screws 150*s* and 150*ss*, as illustrated in FIG. 8, for a selected procedure and/or viewing and understanding by the user 36. The segmentation of the screws 150*s*, 150*ss* is within an image that is not within the training data set 270. Generally, the image segmented by the CNN is an image acquired of the subject 28 by the user 36 after a selected portion of a procedure and after training the CNN.

As discussed above, the CNN that is trained with the training data set 270 that may also include a grade for the selected position of the screw 150 in the patient, which may be determined based upon the segmented screw 150*s*, 150*ss*. Accordingly, the output in block 316 may also include a grade based upon the trained CNN regarding the segmented position of the screws either relative to each other and/or other features in the image 32. It is understood that the CNN may be trained to determine features within the image 32 such as boney structures. Segmentation of boney structures, such as a vertebrae, can include selected known methods. Accordingly, the trained data set 270 that trains the CNN that analyzes the image 32 in block 312, may also be trained with a grade of the position of this screw that is in the image. Thus, the output 316 of the segmentation of the screw images 150*i*, 150*ii* may include a grade for the segmented screws 150*s*, 150*ss* based upon the training data set 270. The user 36, however, may again understand the grade, based upon the CNN analysis of the image 32, and may further apply a manual grade or augmentation to the grade based upon the knowledge and understanding of the user 36.

As discussed above, the member that may include the screw 150 that generates the training data set 270, may be any appropriate member for which the generated simulated image may be made. Thus, the generated simulated image may be based upon any appropriate model such as a hip implant, knee implant, or any other appropriate implant or member that may be appropriately modeled and/or include known components therefore. The generation of the training data set 270 may, therefore, be based upon the generated simulated image at any appropriate member and therefore the segmentation of the screw 150*s* is not limited to screws, but may be segmentation of any appropriate member used to generate the training data set 270. Accordingly, the output 318 may include segmentation of any appropriate member according to a similar process, as discussed above.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of training a neural network, comprising:
- acquiring first image data of a subject taken with an imager having a first imaging modality;
- generating a first simulated model image to simulate an image of a model of a member taken with the first imaging modality based on simulating a projection of x-rays through the model using a predetermined interaction of the x-rays with one or more materials of the member;
- forming an overlayed training image by overlaying the generated first simulated model image on the acquired first image data at a position;
- labeling the overlayed training image;
- grading the overlayed training image based on the position of the first simulated model image on the acquired first image,
  - wherein the grading indicates a value that identifies whether the position of the first simulated model image on the acquired first image is likely to provide a positive result for a related procedure; and
- training the neural network with a training data set that includes the overlayed training image, information associated with the labeling, and information associated with the grading.

2. The method of claim 1, wherein acquiring includes accessing stored image data of the subject, including the first image data.

3. The method of claim 1, wherein the overlayed training image is automatically labeled with the model.

4. The method of claim 1, wherein the model is a three-dimensional model of the member.

5. The method of claim 1, wherein acquiring the first image data of the subject with the first imaging modality comprises:
- projecting x-rays at the subject with the imager; and
- detecting energy with a detector of the imager based on the projected x-rays, wherein the first image modality is x-ray imaging.

6. The method of claim 5, wherein generating the first simulated model image comprises:
- evaluating the model;
- determining an interaction of x-rays with the model if the model were a member in a path of x-rays from a x-ray source to a detector; and
- saving a model image based on the determined interaction of the x-rays with the model, where the model image includes the first simulated model image.

7. The method of claim 6, wherein the determining the interaction of x-rays with the model further comprises accounting for a material within the member.

8. The method of claim 1, wherein the training data set is formed based on:
- forming a plurality of overlayed training images that includes the overlayed training image;
- labeling each overlayed training image of the plurality of the formed overlayed training images; and
- grading each overlayed training image of the plurality of the formed overlayed training images.

9. The method of claim 8, wherein forming the training data set further comprises:

altering the position of the overlayed generated first simulated model image on the acquired first image in each overlayed training image of the plurality of the overlayed training images.

10. The method of claim 8, wherein forming the training data set further comprises:

acquiring a plurality of image data of the subject with the first imaging modality; and forming the plurality of overlayed training images by overlaying the generated first simulated model image on each acquired image data of the plurality of acquired image data at different positions.

11. The method of claim 8, further comprising:

saving the training data set; and accessing the saved training data set to train the neural network by executing instructions with a processor.

12. The method of claim 11, further comprising:

saving the trained neural network.

13. The method of claim 12, further comprising:

segmenting a procedure image not included in the acquired first image data, including segmenting an image of the member in the procedure image.

14. The method of claim 13, further comprising:

displaying the segmented procedure image illustrating the segmented image of the member and highlighting the illustration of the segmented image of the member on a display device.

15. A system for training a neural network, comprising:

a processor operable to execute instructions to:

acquire a first image data of a subject taken with an imager having a first imaging modality;

generate a first simulated model image to simulate an image of a model of a member taken with the first imaging modality based on a simulation of a projection of x-rays through the model using a predetermined interaction of the x-rays with one or more materials of the member;

form an overlayed training image by overlaying the generated first simulated model image on the acquired first image at a position;

label the overlayed training image;

receive information associated with a grade of the overlayed training image, wherein the grade indicates a value that identifies whether the position of the first simulated model image on the acquired first image is likely to provide a positive result;

train the neural network with a data set that includes the overlayed training image, information associated with the label, and the information associated with the grade; and a memory system to store the trained neural network.

16. The system of claim 15, further comprising:

an imaging system to acquire the first image data of the subject.

17. The system of claim 15, further comprising:

a display device to display a segmented procedure image associated with the overlayed training image.

18. A method of training a neural network, comprising:

creating a training data set comprising:

acquiring a first image of a subject with a first imaging modality;

accessing a model of a member having at least a geometry and a material of the member included within the model;

generating a first simulated model image that simulates an image of the member acquired with the first imaging modality based at least on the accessed model of the member based on simulating a projection of x-rays through the accessed model using a predetermined interaction of the x-rays with one or more materials of the member;

forming a first overlayed training image by overlaying the generated first simulated model image on the acquired first image at a first position;

labeling the first overlayed training image; and grading the first overlayed training image, wherein the grading indicates a value that identifies whether the first position of the first simulated model image on the acquired first image is likely to provide a positive result;

accessing the created training data set with a processor to train the neural network with the first overlayed training image, with information associated with the labeling, and with information associated with the grading, at least by determining weights for a neuron within the neural network; and saving the trained neural network for accessing to segment a procedure image.

19. The method of claim 18, wherein creating the data set further comprises:

forming a second overlayed training image by overlaying the generated first simulated model image on the acquired first image at a second position; and labeling the second overlayed training image.

20. The method of claim 18, wherein creating the training data set further comprises:

acquiring a second image data of the subject with the first imaging modality;

forming a second overlayed training image by overlaying the generated first simulated model image on the acquired second image at the first position; and labeling the second overlayed training image.

* * * * *